(12) United States Patent
Stenfors

(10) Patent No.: US 6,309,102 B1
(45) Date of Patent: Oct. 30, 2001

(54) POSITIONER FOR AN X-RAY EXAMINATION APPARATUS

(75) Inventor: Per Stenfors, Spanga (SE)

(73) Assignee: Siemens-Elema AB, Solna (SE)

( * ) Notice: Subject to any disclaimer, the term of this patent is extended or adjusted under 35 U.S.C. 154(b) by 0 days.

(21) Appl. No.: 09/373,717

(22) Filed: Aug. 13, 1999

(30) Foreign Application Priority Data

Aug. 25, 1998 (SE) .................................................. 9802826

(51) Int. Cl.$^7$ .................................................. H05G 1/02
(52) U.S. Cl. .......................... 378/197; 378/193; 378/195; 378/196
(58) Field of Search .................................. 378/193, 195, 378/196, 197

(56) References Cited

U.S. PATENT DOCUMENTS

| | | | |
|---|---|---|---|
| 4,150,297 | 4/1979 | Borggren | 378/181 |
| 4,653,083 | 3/1987 | Rossi | 378/196 |
| 4,922,512 | * 5/1990 | Lajus et al. | 378/197 |
| 4,987,585 | 1/1991 | Kidd et al. | 378/197 |
| 5,038,371 | * 8/1991 | Janssen et al. | 378/197 |
| 5,073,917 | * 12/1991 | Van Endschot et al. | 378/197 |
| 5,095,501 | * 3/1992 | Kobayashi | 378/196 |
| 5,155,757 | * 10/1992 | Sakaniwa et al. | 378/197 |
| 5,367,554 | * 11/1994 | Kobayashi et al. | 378/196 |
| 5,409,497 | 4/1995 | Siczek et al. | 600/407 |
| 6,113,264 | * 9/2000 | Watanabe | 378/197 |
| 6,203,196 | * 3/2001 | Meyer et al. | 378/197 |

FOREIGN PATENT DOCUMENTS

| | | |
|---|---|---|
| 0 333 256 | 9/1989 | (EP) . |
| 0 386 842 | 6/1994 | (EP) . |

* cited by examiner

Primary Examiner—Robert H. Kim
Assistant Examiner—Allen C. Ho
(74) Attorney, Agent, or Firm—Schiff Hardin & Waite

(57) ABSTRACT

An x-ray examination positioner has a base and an arm whose first end is rotatable around a first axle attached in the base and whose second end is connected to a holder in which a curved carrier is displaceably arranged. One end of the carrier carries an x-ray tube and the other end thereof carries an x-ray these being directed toward one another. In combination with an examination table, the carrier can be brought from a head-placed attitude into a vertical side attitude and/or into a lateral position while retaining the imaginary isocenter and, moreover, the physician has very good access to the patient, by rotatably attaching the holder of the carrier to the arm via a second axle. The first axle and the second axle are oriented such that respective imaginary extensions thereof as well as the central ray between the x-ray tube and the receptor intersect at a common point in all attitudes of the arm and of the carrier.

19 Claims, 6 Drawing Sheets

POSITIONER FOR AN X-RAY EXAMINATION APPARATUS

BACKGROUND OF THE INVENTION

1. Field of the Invention

The present invention is directed to an x-ray examination positioning apparatus of the type having a base and an arm with a first end which is rotatable around a first shaft or axle attached in the base and a second end which is connected to a holder in which a curved carrier is displaceably arranged, with an x-ray source mounted at one end of the carrier opposite an x-ray receptor mounted at the other end of the carrier.

2. Description of the Prior Art

An examination table that is displaceable at least in its longitudinal direction is employed in conjunction with x-ray examinations with a positioning apparatus of the aforementioned type. Given, for example, cardiac examinations, it is a great advantage that the curved carrier of the positioner, maintaining its isocenter, can be brought from a position wherein the carrier is in a vertical position behind the head and of the table and wherein the head end is placed between the x-ray tube and the receptor, into a lateral position wherein the carrier is perpendicularly arranged in a vertical position compared to the imaginary center axis of the examination table. Another important advantage is that the carrier, in the described lateral position, can be displaced into another lateral position wherein the central ray of the x-ray tube or of the receptor proceeds in a horizontal plane. Another advantage is that the positioner is fashioned such that the team of physicians has good access to the patient.

An x-ray examination positioning apparatus of the type initially cited is described in the brochure "Advantx L/C" of the GE Medical Systems. The base of the positioner is connected to an L-shaped arm having one leg proceeding along the floor. The axis of the fastening device, around which the arm and the base are rotatable, is attached to the floor below the head end of the examination table. The holder, wherein the carrier for the x-ray tube and the receptor is displaceably arranged, is rigidly connected to an upright leg of the arm. As a result of the leg that extends under the table and as a result of the fastening means, the positioner together with the carrier for the x-ray tube and the receptor can be rotated from a position wherein the carrier is attached to the head end of the table into a further position wherein the carrier is arranged at an angle of 90° relative to the longitudinal direction of the table. The positioner is also constructed such that the center line between the x-ray tube and the receptor is in axial alignment with the axis of the fastening means given a vertical setting. This is achieved by the x-ray tube and the receptor being connected to the carrier via a boom. As a result, the x-ray tube and the receptor are always rotated around the same point when rotating the positioner around the axis of the fastening device. Since the arm at the floor in the area of the axis of the fastening device is comparatively wide and high, however, the physician may accidentally hit the floor arm with his or her feet during the examination, this being potentially disturbing. Due to the position and thickness of the arm, the carrier for the x-ray tube and the receptor cannot be lowered down to the floor given a vertical attitude. Given such a vertical attitude, the lowering of the x-ray tube and of the receptor by 4 through 5 cm, which is approximately the thickness of the arm, can be critical in order to obtain a good working height for the team of physicians. A further disadvantage is that the carrier can be turned into a lateral position only ±45°. A lateral position is achieved only in combination with a head position. The inside dimension of the curved carrier determines how far the x-ray tube can sweep when the head end of the table is placed within the carrier maximally close to the holder. This is a limitation of the setting possibilities of the x-ray tube and of the receptor. This known positioner, moreover, is relative complicated in terms of structure and the floor arm, the fastening device and the boom of the x-ray tube and of the receptor limit access to the patient.

European Application 0 386 842 discloses an x-ray examination positioner having a base firmly connected to the floor, an L-shaped arm arranged at the base and rotatable around a shaft, and a carrier for an x-ray tube and a receptor arranged at the free end of the arm. The carrier is rotatably secured directly to the arm via an axle. As a result of this structure, the imaginary axle extensions as well as the central ray between the x-ray tube and the receptor intersect in a common point. Because the carrier for the x-ray tube and the receptor, however, is rotatably attached directly to the arm, the positioner exhibits certain limitations in terms of its motion pattern. Thus, for example, the carrier cannot be shifted into what is referred to as a head-placed attitude that has just been described. In an exemplary embodiment described in said European Application, a holder for an arcuate carrier is provided that is firmly connected to the free end side of the arm such that the holder and the carrier form an extension of the arm. In order to compensate the L-shaped arm such that the imaginary extension of the base axle intersects the central ray of the x-ray tube and of the receptor, the x-ray tube and the receptor are connected to the carrier via booms. As a result of this structure, the carrier cannot undertake a spherical movement around a desired point. The carrier also cannot assume a lateral position that is perpendicular in relationship to the examination table, since the arm together with the carrier proceeds parallel to the examination table in all attitudes.

SUMMARY OF THE INVENTION

An object of the present invention is to provide an x-ray examination positioning apparatus of the type initially described that is comparatively simple in structure and wherein, in conjunction with an examination table, the carrier can be brought from what is referred to as a head-positioned attitude, i.e. a position wherein the carrier is placed in a vertical position behind the head end of the table, into a vertical lateral position and/or into a lateral position while retaining the imaginary isocenter. Moreover, the physician should have very good access to the patient.

This object is inventively achieved in a positioning apparatus wherein an arm is rotatably attached to a base via a first axle and the holder of the carrier is rotatably connected to the arm via a second axle, and wherein the center axis of the first axle (imaginarily extending beyond the end of the first axle) and a center axis of the second axle (imaginarily extending beyond an end of the second axle), as well as a central ray proceeding between the x-ray tube or and the receptor intersect a common point in all positions of the arm and the carrier. Because the holder for the carrier is rotatably connected to the arm and as a result of the mutual arrangement of the axles, a positioner is achieved that is very simple in structure, the arcuate carrier thereof enabling a spherical movement around a point in space without having to displace the base. This means that the carrier of the positioner, in conjunction with an examination table, can be brought— while retaining the isocenter—from a head-placed attitude into a vertical side attitude and/or into a lateral position.

In an embodiment of the invention, the imaginary extension of the first axle describes an angle with a horizontal plane, for example a floor. This allows the carrier, particularly in conjunction with a lateral attitude, to be lowered down to the floor, providing the advantage that the working height (the table height) can be lowered to a position that is optimum for the team of physicians. A further advantage is that the radius of the carrier can be comparatively large.

The first axle can also proceed parallel to a horizontal plane, for example a floor.

According to the invention, the base is firmly attached to the floor or to the ceiling.

In another embodiment of the inventive positioner in conjunction with an examination table, the base is arranged such that the first axle for the base and the arm and the imaginary extension thereof describes an angle—as viewed from above—with the central axis of the examination table. The angle can amount to between 5° and 85°, preferably 40°. This allows the base to be attached outside the actual area around the examination table, giving the physician extremely good access to the patient.

In a further embodiment of the inventive positioner wherein the base is secured to the floor, the imaginary extension of the first axle intersects the common point—viewed from the side—at an angle relative to the floor of between 10° and 35°, preferably 21°, from below. As a result of such an angle of the shaft, an extremely compact base, whose height is lower then the height of the examination table is obtained.

In another embodiment of the invention, the length of the arm is adjustable. Such an adjustment can be advantageous, particularly when the carrier has a lateral attitude. Given an extension of the arm in this lateral attitude, an increase in the range is established. An adjustable arm can also be advantageous when the positioner is brought into a standby position, i.e. when the arm and the carrier are removed from the patient area.

The arm of the invention also can be attached to the base so as to be displaceable in its longitudinal direction. Among other things, the aforementioned advantages are thus obtained.

DESCRIPTION OF THE PREFERRED EMBODIMENTS

Figure 1:
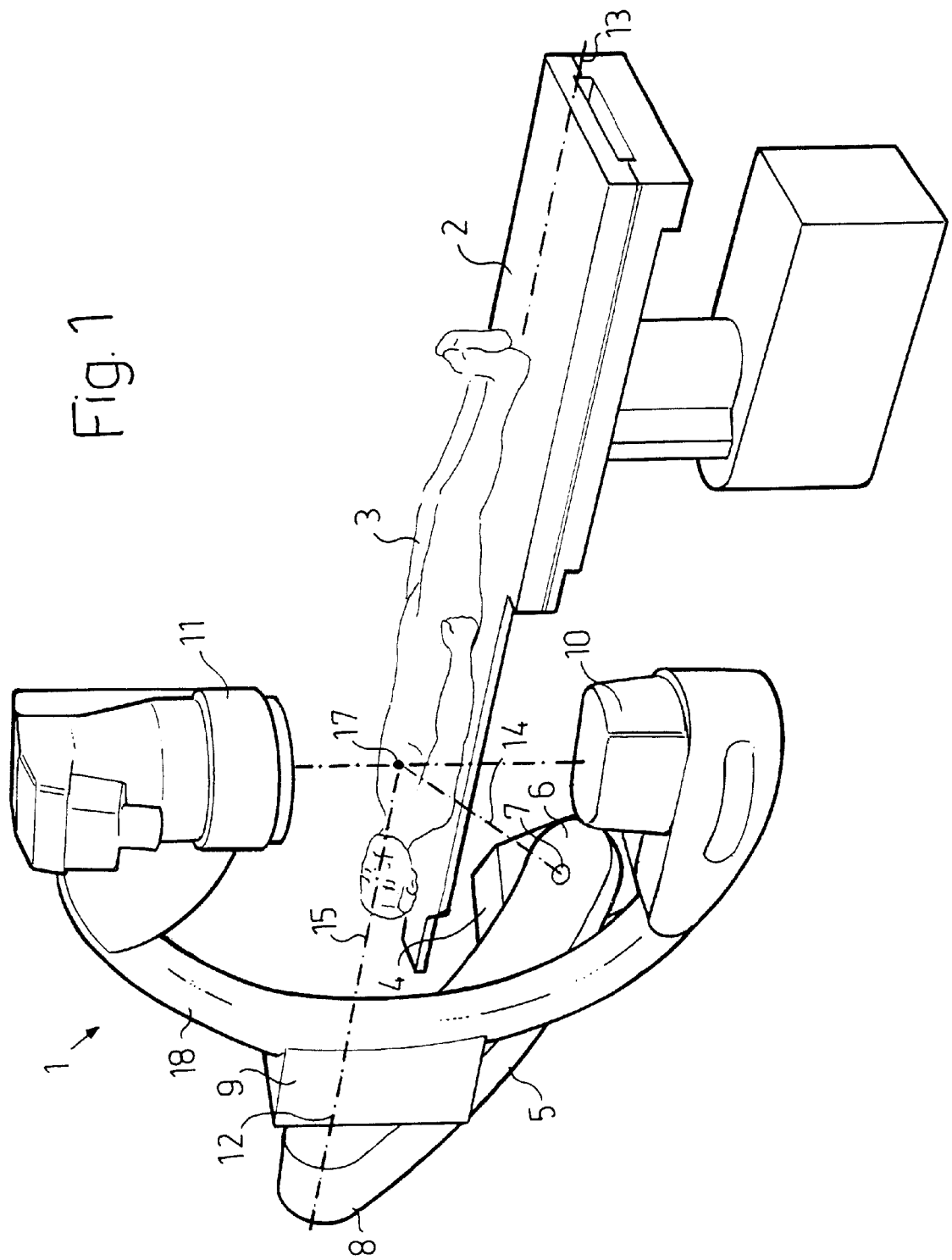
FIG. 1 is a perspective view of an x-ray examination apparatus with a positioner according to the invention, and an examination table, the positioner having a carrier for the x-ray tube and the receptor in a head-placed attitude relative to the examination table.

FIG. 1 shows an x-ray examination apparatus with a positioner 1 and an examination table 2 on which a patient 3 is supported. The examination table, which is secured to the floor in this exemplary embodiment, is displaceable at least in its longitudinal direction along a center axis 13. The positioner 1 has a base 4 and an arm 5 whose first end 6 is mounted so as to be rotatable around a first axle 7 arranged in the base 4. The second end 8 of the arm 5 is connected to a holder 9 in which a C arm carrier 18 is displaceably arranged. One end of the carrier 18 has an x-ray tube/diaphragm 10 mounted thereto and the other end has an x-ray with a receptor 11 mounted thereto, these being directed toward one another. The holder is rotatably connected to the arm 5 via a second axle 12.

It is shown in FIG. 1 that the first axle 7 and the second axle 12 oriented such that respective imaginary extensions 14,15 thereof as well as the central ray between the x-ray tube/diaphragm 10 and the receptor 11, intersect a common point 17. As a result at the arm 5 can be rotated around the axle 7, the holder 9 around the axle 12 and the carrier 18 can be displaced in the holder 9. Also, as a result thereof, the position of the point 17 in space can be retained when the x-ray tube/diaphragm 10 and the receptor 11 are displaced into various positions of interest for x-ray exposures. The rotation of the arm 5 and the holder 9 and the displacement of the carrier 18 in the holder 9 ensue in a known way with the assistance of motors that are not shown.

It is also shown in FIG. 1 that the base 4 of the positioner 1 is secured to the floor outside the immediate area of around the examination table. To be more exact, the base 4 is arranged such that the axle 7 and its imaginary shaft extension 14—viewed from above-describes an angle with the center axis 13 of the examination table 2 that can be between 5° and 85°, preferably 40°. It is also shown that the imaginary extension 14 of the axle 7 intersects the common point 17 from below with an angle relative to the floor between 10° and 35°, preferably 21°. A very low base 4 is thus obtained, this being significantly lower then the height of the examination table 2. In FIG. 1, the carrier 18 of the positioner 1 is shown in a head-placed attitude wherein the carrier 18 is located in a vertical position behind the head end of the examination table 2 and the head end is located in the carrier 18. In the exemplary embodiment shown in the FIG. 1, the point 17 around which the carrier 18 is turned is placed in the heart or in the proximity of the heart.

Figure 2:
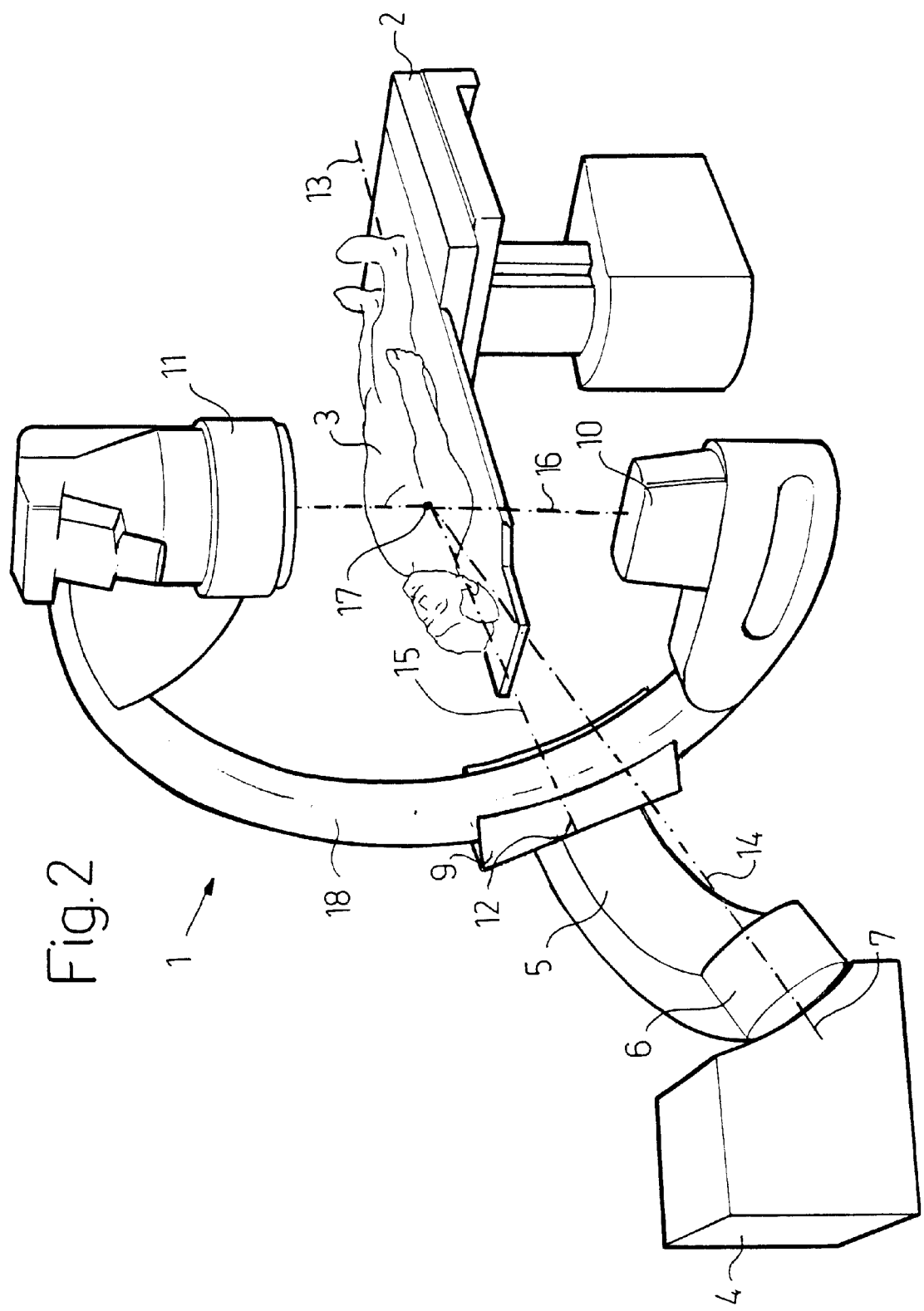
FIG. 2 shows an x-ray examination apparatus with a positioner according to FIG. 1, with the carrier in a vertical attitude and perpendicularly arranged relative to the longitudinal direction of the table.
Figure 3:
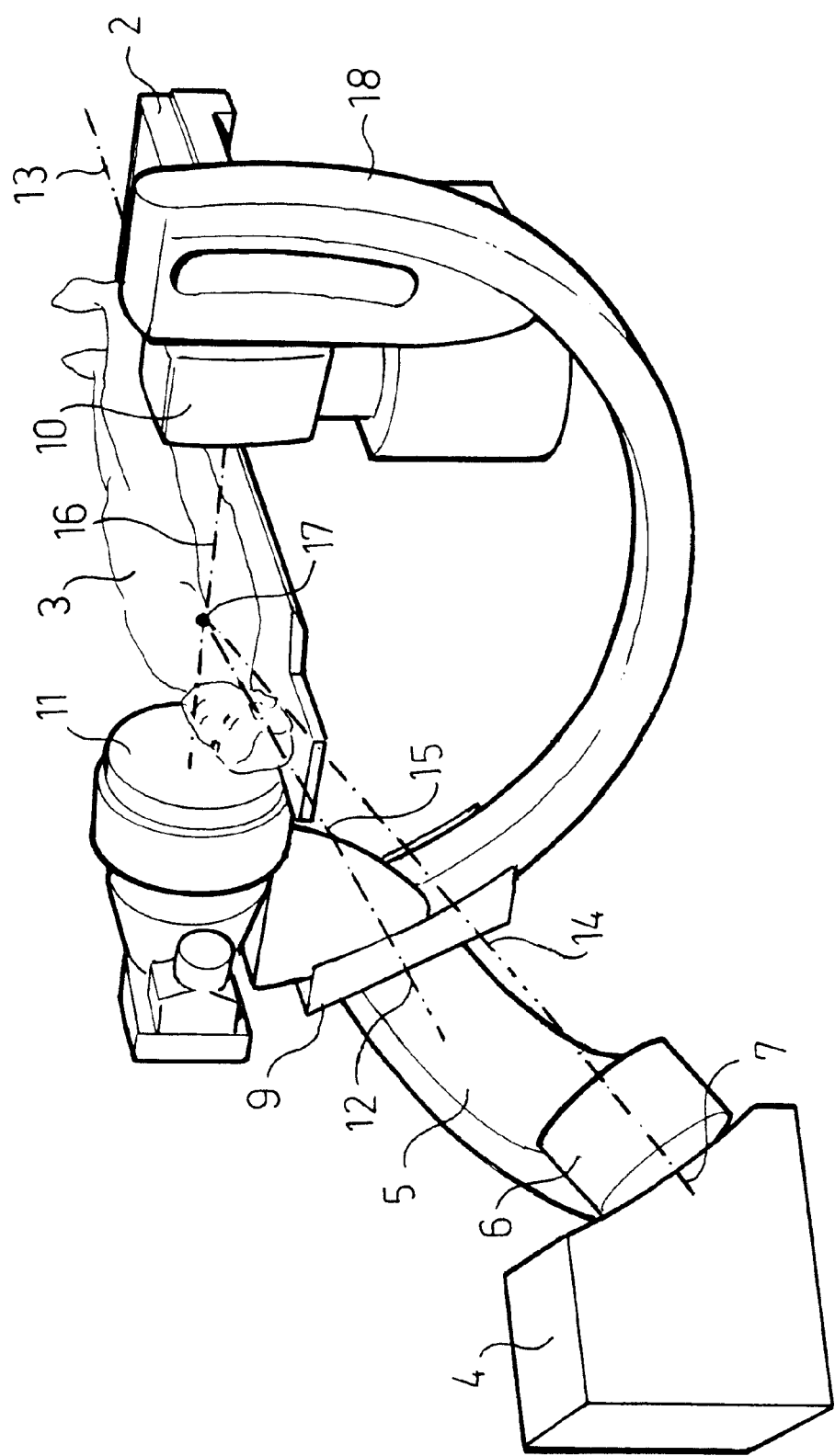
FIG. 3 shows an x-ray examination apparatus with a positioner, and an examination table, according to FIG. 1 with the carrier in a lateral attitude.

Retaining the isocenter (point 17), the carrier 18 can now be rotated in the described way from a head-placed attitude into a side attitude wherein the carrier 18 is perpendicularly arranged in a vertical position relative to the imaginary center axis 13 of the examination table 2. Such a side attitude is shown in FIG. 2. In FIG. 2 the angle of the axle 7 and the imaginary extension 14 thereof relative to the horizontal plane, the floor here, is clearly shown. The carrier 18 can now be displaced into a lateral attitude with the assistance of a motor (not shown) by displacing the carrier 18 in the holder 9 from a position shown in FIG. 2. This is shown in FIG. 3. The structure of the positioner 1 makes it possible here for the carrier 9 to be attached under the table 2, producing significant advantages in conjunction with access to the patient 3. Since no disturbing parts of the positioner 1 are present under the table 2, the carrier 18 can be lowered virtually down to the floor by arm 5, so that the isocenter (point 17) can be selected such that an optimum working height is established.

Figure 4:
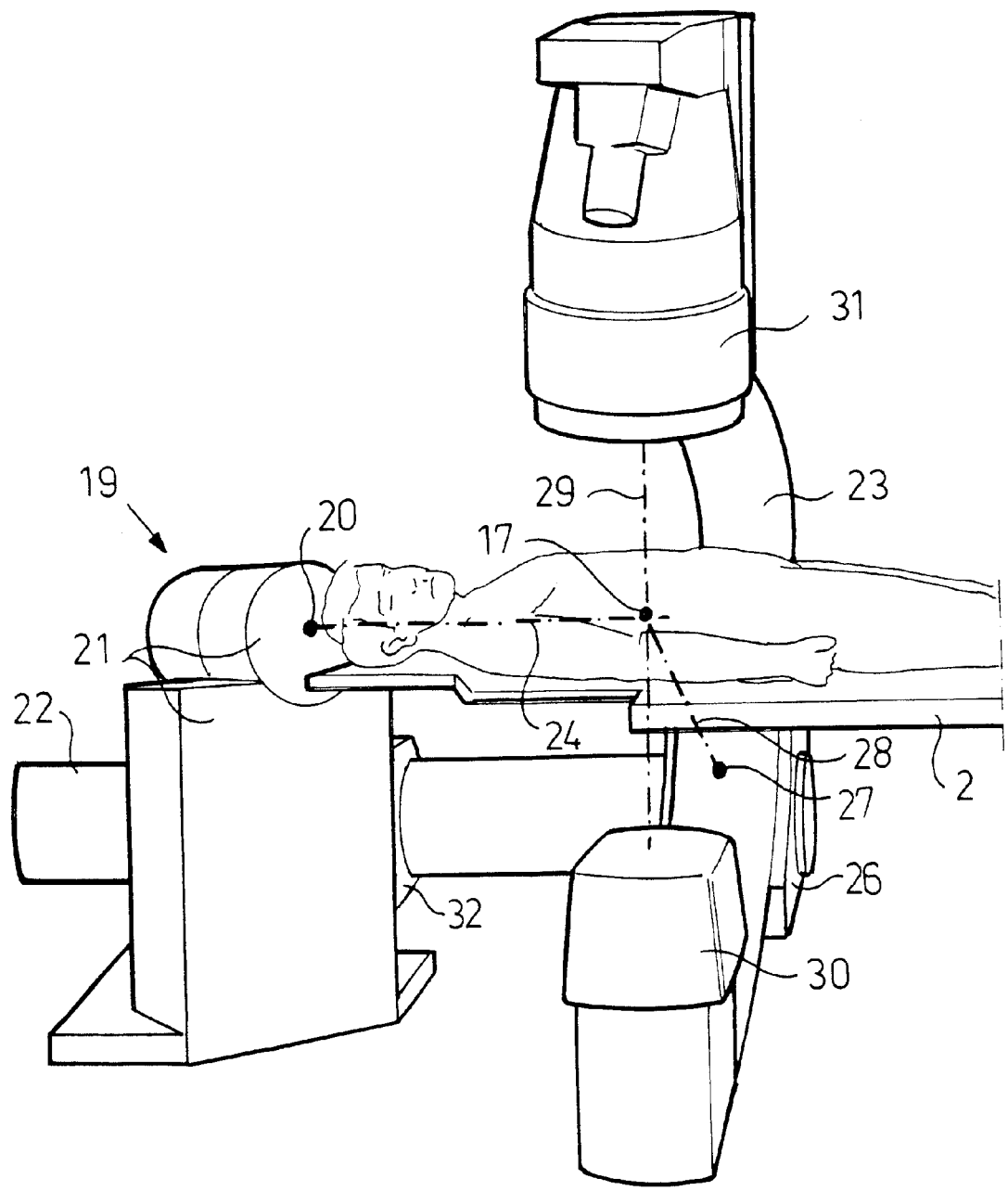
FIG. 4 is a side view of an x-ray examination apparatus with a positioner of the invention in a further embodiment.

FIG. 4 shows a positioner 19 that differs from the positioner 1 in that the axle 20 for the base 21 and for the arm 22 proceeds parallel to the floor. In this exemplary embodiment, the base 21 lies approximately at the level of the examination table 2. The axle 20 and the imaginary extension 24 thereof always exhibit the same height as the point 17 around which the positioner 19 can be rotated. FIG. 4 shows that the arm 22 is displaceable in its longitudinal direction in a profiled holder 32 that is rotatably connected to the base 21 via the axle 20. The arm 22 can be displaced with the assistance of a motor that is not shown. This is of particular interest in those instances wherein an angiography examination is undertaken and contrast agent is injected into the patient. The team of physicians can track the course of the contrast agent in the patient with the assistance of the displaceable arm 22.

Figure 5:
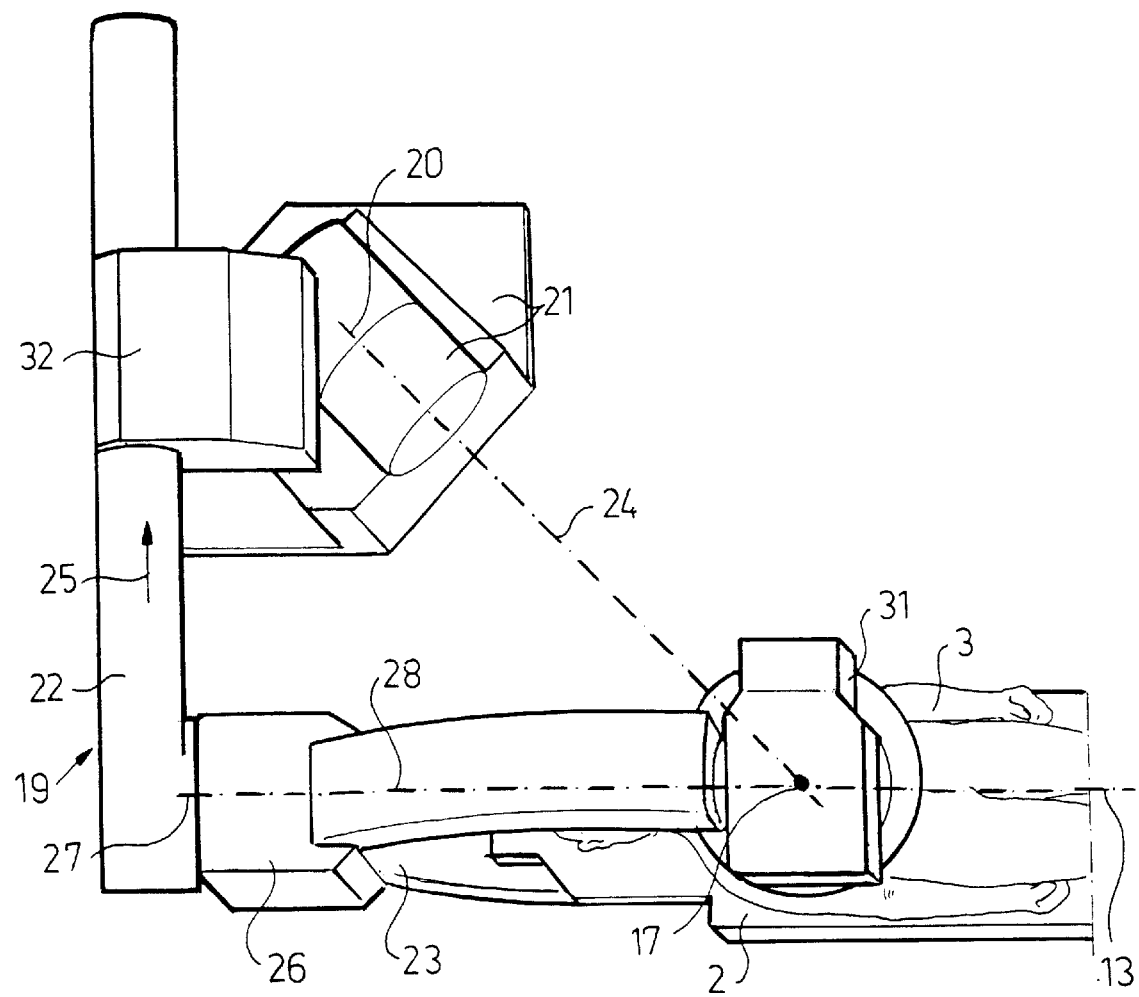
FIG. 5 is a plan view of the x-ray examination apparatus according to FIG. 4.

In FIG. 5, which is a plan view of the positioner 19 and of the examination table 2 with the patient 3, it is shown that the axle 20 and the imaginary extension 24 thereof describe an angle with the center axis 13 of the examination table 2. In FIG. 5, the carrier 23 is shown in a vertical head-placed attitude. As shown in FIG. 5 the arm 22, which is displaceable in the profiled holder 32, can be of use when parking the positioner 19, since the arm 22 as well as the carrier 23 can be moved away from the immediate area around the examination table 2. The arrow 25 shows the direction of displacement of the arm 22 and of the carrier 23 for a parking (standby) position. In FIGS. 4 and 5, the holder of the carrier 23 is referenced 26, the second axle is referenced 27, the imaginary extension thereof is referenced 28, the central ray is referenced 29 and the x-ray tube/diaphragm is referenced 30 and the receptor is referenced 31.

The arm 22 of the positioner 19 and the arm 5 of the positioner 1 can also be adjustable in their longitudinal directions, such as by being fashioned as telescoping arms.

Figure 6:
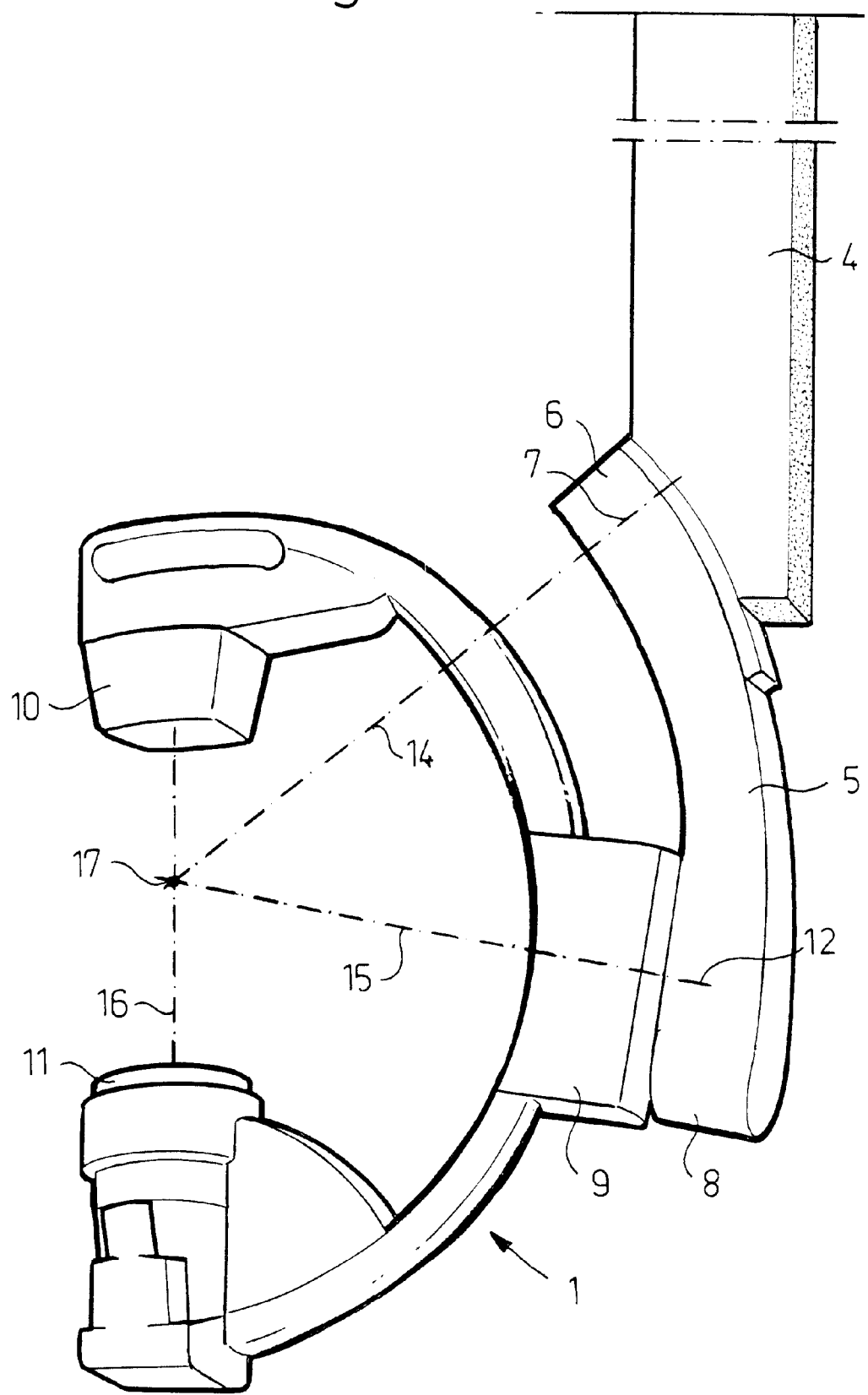
FIG. 6 shows a positioner according to FIGS. 1 through 3 that is secured to a ceiling.

FIG. 6 shows a ceiling-mounted positioner 1 with a base 4 secured to the ceiling and adapted in height. Otherwise, the positioner 1 is constructed as was described in conjunction with FIGS. 1 through 3. It is important that the imaginary extension 14 of the axle 7 for the base 4 and the arm 5 is arranged such that it describes an angle with a horizontal plane, with the ceiling in this case.

As a result of the invention, an x-ray examination apparatus is obtained with a positioner that is simple in structure and compact due to the relatively low base, and whose carrier for the x-ray tube/diaphragm and the receptor can be rotated around a desired fixed point in space from, for example, a head-placed attitude into an already described lateral attitude and can be turned further into a lateral position. The inside radius of the carrier can be made comparatively large since no parts of the positioner are arranged under the table. As a result, the x-ray tube and the receptor can sweep the torso of the patient comparatively extensively given a head-placed attitude. As a result of the comparatively large radius of the carrier and because the base can be placed outside the patient area, good access to the patient is established.

Although other modifications and changes may be suggested by those skilled in the art, it is the intention of the inventors to embody within the patent warranted hereon all changes and modifications as reasonably and properly come within the scope of their contribution to the art.

I claim as my invention:

1. A positioner for an x-ray examination apparatus, said positioner comprising:
    a base;
    an arm having a first end and a second end;
    a first axle rotatably connecting said first end of said arm to said base;
    a curved carrier having a first end at which an x-ray tube is mounted and a second end at which an x-ray receiver is mounted facing said x-ray tube with a central x-ray proceeding between said x-ray tube and said x-ray receiver;
    a holder in which said curved carrier is displaceably mounted;
    a second axle rotatably connecting said second end of said arm to said holder; and
    an imaginary extension of said first axle and an imaginary extension of said second axle both intersecting said central ray at a common point in all positions of said arm and said carrier, said first axle being oriented so that said imaginary extension of said first axle forms an acute angle with a horizontal plane.

2. A positioner as claimed in claim 1 further comprising means adapted for attaching said base to a floor.

3. A positioner as claimed in claim 1 further comprising means adapted for attaching said base to a ceiling.

4. A positioner for an x-ray examination apparatus, said positioner comprising:
    a base;
    an arm having a first end and a second end;
    a first axle rotatably connecting said first end of said arm to said base;
    a curved carrier having a first end at which an x-ray tube is mounted and a second end at which an x-ray receiver is mounted facing said x-ray tube with a central x-ray proceeding between said x-ray tube and said x-ray receiver;
    a holder in which said curved carrier is displaceably mounted;
    a second axle rotatably connecting said second end of said arm to said holder; and
    an imaginary extension of said first axle and an imaginary extension of said second axle both intersecting said central ray at a common point in all positions of said arm and said carrier, said first axle being oriented parallel to a horizontal plane.

5. A positioner as claimed in claim 4 further comprising means adapted for attaching said base to a floor.

6. A positioner as claimed in claim 4 further comprising means adapted for attaching said base to a ceiling.

7. A positioner for an x-ray examination apparatus, said positioner comprising:
    an examination table having a longitudinal center axis and being displaceable along said longitudinal center axis;
    a base;
    an arm having a first end and a second end;
    a first axle rotatably connecting said first end of said arm to said base; a curved carrier having a first end at which an x-ray tube is mounted and a second end at which an x-ray is mounted facing said x-ray tube with a central x-ray proceeding between said x-ray tube and said x-ray receiver;
    a holder in which said curved carrier is displaceably mounted;
    a second axle rotatably connecting said second end of said arm to said holder; and
    an imaginary extension of said first axle and an imaginary extension of said second axle both intersecting said central ray at a common point in all positions of said arm and said carrier, said base being oriented so that said first axle and said imaginary extension of said first axle form an acute angle with said longitudinal center axis.

8. A positioner as claimed in claim 7 wherein said angle comprises an angle in a range between 5° and 85°.

9. A positioner as claimed in claim 8 wherein said angle is 40°.

10. A positioner as claimed in claim 7 further comprising means adapted for attaching said base to a floor, and wherein said first axle is oriented so that said imaginary extension of said first axle, as seen from a side, intersects said common point from below at an angle relative to the floor in a range between 10° and 35°.

11. A positioner as claimed in claim 10 wherein said angle relative to the floor is 21°.

12. A positioner as claimed in claim 7 further comprising means adapted for attaching said base to a floor.

13. A positioner as claimed in claim 7 further comprising means adapted for attaching said base to a ceiling.

14. A positioner for an x-ray examination apparatus, said positioner comprising:
    a base;
    an adjustable-length arm having a first end and a second end;
    a first axle rotatably connecting said first end of said arm to said base; a curved carrier having a first end at which an x-ray tube is mounted and a second end at which an x-ray is mounted facing said x-ray tube with a central x-ray proceeding between said x-ray tube and said x-ray receiver;
    a holder in which said curved carrier is displaceably mounted;
    a second axle rotatably connecting said second end of said arm to said holder; and
    an imaginary extension of said first axle and an imaginary extension of said second axle both intersecting said central ray at a common point in all positions of said arm and said carrier.

15. A positioner as claimed in claim 14 further comprising means adapted for attaching said base to a floor.

16. A. A positioner as claimed in claim 14 further comprising means adapted for attaching said base to a ceiling.

17. A positioner for an x-ray examination apparatus, said positioner comprising:
    a base;
    an arm having a first end and a second end; and
    a longitudinal axis;
    means for attaching said arm to said base for allowing displacement of said arm along said longitudinal axis a first axle rotatably connecting said first end of said arm to said base; a curved carrier having a first end at which an x-ray tube is mounted and a second end at which an x-ray is mounted facing said x-ray tube with a central x-ray proceeding between said x-ray tube and said x-ray receiver;
    a holder in which said curved carrier is displaceably mounted;
    a second axle rotatably connecting said second end of said arm to said holder; and
    an imaginary extension of said first axle and an imaginary extension of said second axle both intersecting said central ray at a common point in all positions of said arm and said carrier.

18. A positioner as claimed in claim 17 further comprising means adapted for attaching said base to a floor.

19. A positioner as claimed in claim 17 further comprising means adapted for attaching said base to a ceiling.

* * * * *